United States Patent
Ushiro et al.

(10) Patent No.: US 10,308,745 B2
(45) Date of Patent: Jun. 4, 2019

(54) COPOLYMER AND MEDICAL DEVICE, SEPARATION MEMBRANE MODULE FOR MEDICAL USE, AND BLOOD PURIFIER INCLUDING THE SAME

(71) Applicant: Toray Industries, Inc., Tokyo (JP)

(72) Inventors: Suguru Ushiro, Otsu (JP); Hiroshi Takahashi, Otsu (JP); Yoshiyuki Ueno, Otsu (JP)

(73) Assignee: Toray Industries, Inc. (JP)

( * ) Notice: Subject to any disclaimer, the term of this patent is extended or adjusted under 35 U.S.C. 154(b) by 112 days.

(21) Appl. No.: 15/556,002

(22) PCT Filed: Mar. 15, 2016

(86) PCT No.: PCT/JP2016/058162
§ 371 (c)(1),
(2) Date: Sep. 6, 2017

(87) PCT Pub. No.: WO2016/158388
PCT Pub. Date: Oct. 6, 2016

(65) Prior Publication Data
US 2018/0162977 A1 Jun. 14, 2018

(30) Foreign Application Priority Data

Mar. 31, 2015 (JP) .................. 2015-072340

(51) Int. Cl.

| | |
|---|---|
| C08F 226/10 | (2006.01) |
| B01D 71/44 | (2006.01) |
| B01D 71/68 | (2006.01) |
| A61K 35/16 | (2015.01) |
| A61M 1/16 | (2006.01) |
| A61M 1/34 | (2006.01) |
| B01D 71/76 | (2006.01) |
| C09D 139/06 | (2006.01) |
| C08F 218/10 | (2006.01) |
| B01D 67/00 | (2006.01) |
| B01D 69/06 | (2006.01) |
| B01D 69/08 | (2006.01) |
| A61L 33/06 | (2006.01) |
| C08F 226/06 | (2006.01) |
| B01D 71/38 | (2006.01) |

(52) U.S. Cl.
CPC ............ *C08F 226/10* (2013.01); *A61K 35/16* (2013.01); *A61L 33/064* (2013.01); *A61M 1/16* (2013.01); *A61M 1/34* (2013.01); *B01D 67/009* (2013.01); *B01D 67/0088* (2013.01); *B01D 69/06* (2013.01); *B01D 69/08* (2013.01); *B01D 71/44* (2013.01); *B01D 71/68* (2013.01); *B01D 71/76* (2013.01); *C08F 218/10* (2013.01); *C09D 139/06* (2013.01); *A61M 2205/7563* (2013.01); *B01D 71/38* (2013.01); *C08F 226/06* (2013.01)

(58) Field of Classification Search
USPC .................................................. 525/189, 190
See application file for complete search history.

(56) References Cited

U.S. PATENT DOCUMENTS

| | | |
|---|---|---|
| 2003/0162905 A1 | 8/2003 | Benz et al. |
| 2004/0127390 A1 | 7/2004 | Macnab et al. |
| 2008/0093586 A1 | 4/2008 | Koch et al. |
| 2011/0017654 A1 | 1/2011 | Ueno et al. |

FOREIGN PATENT DOCUMENTS

| | | | |
|---|---|---|---|
| CN | 10289859 A | * 9/2012 | ............ C08F 283/02 |
| JP | 63-53465 A | 3/1988 | |
| JP | 6-238139 A | 8/1994 | |
| JP | 8-254833 A | 10/1996 | |
| JP | 2005-518841 A | 6/2005 | |
| JP | 2008-510602 A | 4/2008 | |
| JP | 2009-262147 A | 11/2009 | |
| JP | 2013-521363 A | 6/2013 | |
| JP | 2014-42913 A | 3/2014 | |

* cited by examiner

*Primary Examiner* — Terressa Boykin
(74) *Attorney, Agent, or Firm* — DLA Piper LLP (US)

(57) ABSTRACT

A copolymer has blood compatibility and antithrombotic properties of greatly suppressing protein adhesion to be usable even when in contact with a biological component such as blood for a long period of time, and a medical device uses the copolymer. The copolymer is characterized by including a hydrophilic unit and a hydrophobic unit, wherein the hydrophobic unit contains at least one type of a carboxylic acid vinyl unit, and the number of carbon atoms at the terminal of a side chain of the carboxylic acid vinyl unit is 2-7.

14 Claims, 1 Drawing Sheet

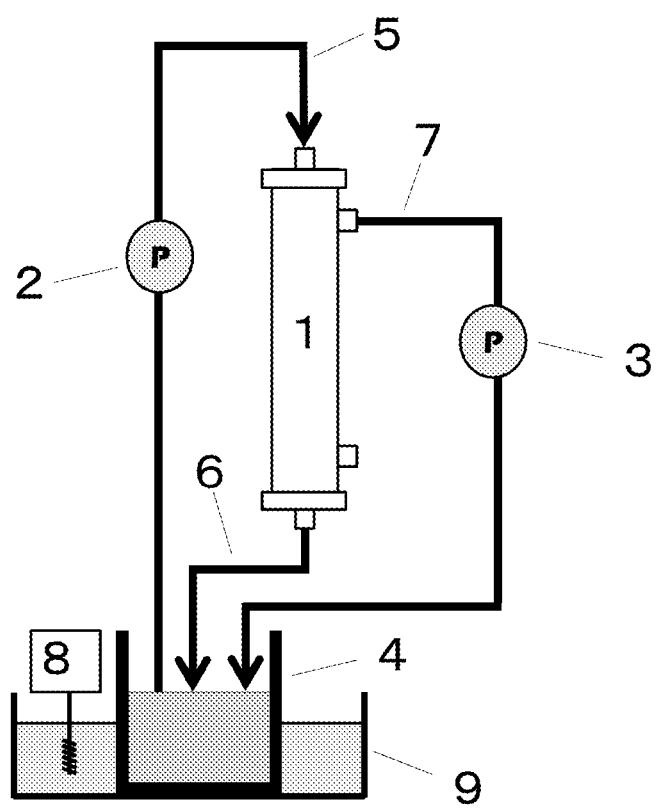

COPOLYMER AND MEDICAL DEVICE, SEPARATION MEMBRANE MODULE FOR MEDICAL USE, AND BLOOD PURIFIER INCLUDING THE SAME

TECHNICAL FIELD

This disclosure relates to a copolymer capable of suppressing adhesion of platelets and proteins even when used in contact with a biological component such as blood for a long period of time, and a medical device, a separation membrane module for medical use, and a blood purifier including the copolymer.

BACKGROUND

When a biological component such as blood or a body fluid comes into contact with a surface of a material used in a medical device, the material is recognized as a foreign matter and causes adhesion of platelets and proteins, deterioration of material performance, and even biological reactions to lead to serious problems. For example, in a blood purifier, adhesion of proteins and platelets deteriorates fractionation performance and water permeability. In particular, in a continuous renal replacement type blood purifier used for the treatment of acute renal failure, it is important to suppress adhesion of platelets and proteins and prolong the usable time of the blood purifier because the blood purifier is continuously used for one day to several days. To deal with such an issue, attempts have been made to make the surface of a material used in a medical device hydrophilic, and various studies have been made.

For example, a method is known in which polyvinylpyrrolidone, which is a hydrophilic polymer, is mixed in polysulfone at the stage of a membrane-forming stock solution and the resultant mixture is molded so that hydrophilicity is imparted to the membrane and contamination is suppressed. However, that method has restrictions in that a large amount of a hydrophilic polymer should be incorporated into the membrane-forming stock solution to impart hydrophilicity to the surface, and the hydrophilic polymer is limited to a polymer compatible with the base polymer.

Meanwhile, Japanese Patent Laid-open Publication No. 6-238139 discloses a method of bringing a polysulfone-based separation membrane into contact with a solution of a hydrophilic polymer such as polyvinylpyrrolidone, and then forming a coating layer insolubilized by radiation crosslinking.

In addition, Japanese Patent Laid-open Publication No. 2009-262147 and Published Japanese Translation No. 2005-518841 disclose a method of introducing a copolymer composed of a hydrophilic unit and a hydrophobic unit typified by a vinylpyrrolidone/vinyl acetate copolymer onto the surface.

The method described in Japanese Patent Laid-open Publication No. 6-238139, however, has a problem that it is difficult to form a coating layer because the interaction between a hydrophilic polymer such as polyvinylpyrrolidone and a polysulfone-based polymer that is a hydrophobic polymer is weak.

On the other hand, in the methods described in Japanese Patent Laid-open Publication No. 2009-262147 and Published Japanese Translation No. 2005-518841, a hydrophobic unit interacts with a hydrophobic base material, whereby the introduction efficiency of the copolymer is increased and the surface can be efficiently hydrophilized. Therefore, it is clear that the methods suppress the adhesion of platelets and proteins as compared to when only a hydrophilic polymer such as polyvinylpyrrolidone is introduced onto the surface.

Even in the methods described in Japanese Patent Laid-open Publication No. 2009-262147 and Published Japanese Translation No. 2005-518841, however, when the copolymer is used in a medical device to be used in contact with a biological component such as blood for a long period of time as in a continuous renal replacement type blood purifier, blood coagulation and protein adhesion progress with time due to the long-time contact with the biological component such as blood, which may eventually lead to clogging and render the medical device unusable.

It could therefore be helpful to provide an anti-thrombotic copolymer capable of suppressing adhesion of platelets and proteins even when in contact with a biological component such as blood for a long period of time, and a medical device, a separation membrane module for medical use, and a blood purifier including the copolymer that are high in blood compatibility.

SUMMARY

Proteins contained in biological components such as blood are likely to adhere to hydrophobic surfaces. Accordingly, it is considered important that the entire contact surface of a medical device is hydrophilic. This is thought to be due to the fact that adhesion of proteins to the material surface changes the higher order structure of the proteins to expose the hydrophobic site present inside, and such hydrophobic site interacts hydrophobically with the material surface.

Even if the surface is coated with a hydrophilic polymer such as polyethylene glycol or polyvinyl alcohol, however, adhesion of proteins and the like cannot be suppressed. This is thought to be due to the fact that if the surface of a medical device is too hydrophilic, adsorbed water with low mobility present on the surface destabilizes the structure of the proteins and the proteins are trapped on the surface so that adhesion of the proteins cannot be sufficiently suppressed.

Therefore, a method has been developed in which a copolymer obtained by copolymerizing a hydrophilic monomer such as vinylpyrrolidone or polyvinyl alcohol with a hydrophobic monomer such as polyethylene or vinyl acetate is allowed to be present on the surface. It is known that this method can efficiently suppress adhesion of proteins and platelets. However, even in such copolymer, when the copolymer is used in a medical device used in contact with a biological component such as blood for a long period of time as in a continuous renal replacement type blood purifier, there are cases where the resistance to blood coagulation or protein adhesion is insufficient.

In view of the above-mentioned circumstances, we found that the design of the side chain structure of a copolymer is important in suppressing blood coagulation and protein adhesion for a long period of time. We found that use of a bulky substituent in the side chain of the hydrophobic unit can suppress the interaction between the hydrophilic unit and water around the copolymer and suppress the adhesion of proteins for a long period of time.

That is, we found that our anti-thrombotic copolymer which maintains blood compatibility and protein adhesion suppression, and a medical device including the copolymer are achieved by the following (1) to (13):

(1) A copolymer including a hydrophilic unit and a hydrophobic unit,
wherein the hydrophobic unit includes at least one vinyl carboxylate unit, and the vinyl carboxylate unit has 2 or more and 7 or less carbon atoms at a side chain terminal thereof.
(2) The copolymer according to the above (1), wherein the hydrophilic unit includes a vinylpyrrolidone unit.
(3) The copolymer according to the above (1) or (2), having a number average molecular weight of 2,000 or more.
(4) The copolymer according to any one of the above (1) to (3), wherein the hydrophilic unit has a mole fraction to the whole copolymer of 30% or more and 90% or less.
(5) The copolymer according to any one of the above (1) to (4), wherein the hydrophilic unit and the hydrophobic unit are arranged randomly or alternately.
(6) The copolymer according to any one of the above (1) to (5), which is used in a medical device.
(7) A medical device including the copolymer according to any one of the above (1) to (6).
(8) The medical device according to the above (7), including the copolymer introduced onto at least a part of a surface thereof that is in contact with a biological component.
(9) A separation membrane module for medical use, including a separation membrane including the copolymer according to any one of the above (1) to (6).
(10) The separation membrane module for medical use according to the above (9), wherein the separation membrane includes a polysulfone-based polymer as a main raw material.
(11) A blood purifier including the copolymer according to any one of the above (1) to (6).
(12) The blood purifier according to the above (11), which is of a continuous renal replacement type.
(13) The blood purifier according to the above (11) or (12), including the copolymer introduced onto at least a part of a surface thereof that is in contact with blood or a biological component.

Our copolymer can suppress adhesion of platelets and proteins even when used in contact with a biological component such as blood for a long period of time. Furthermore, the medical device, the separation membrane module for medical use, and the blood purifier suppress the gradual adhesion of platelets and proteins even when used in contact with a biological component such as blood, and can be used for a long period of time.

BRIEF DESCRIPTION OF THE DRAWING

FIG. 1 is a schematic diagram of a circuit used to measure the temporal change of a sieving coefficient of albumin.

DESCRIPTION OF REFERENCE SIGNS

1: Hollow fiber membrane module
2: Bi pump
3: F pump
4: Circulation beaker
5: Bi circuit
6: Bo circuit
7: F circuit
8: Heater
9: Warm water bath

DETAILED DESCRIPTION

Our copolymer is a copolymer including a hydrophilic unit and a hydrophobic unit, wherein the hydrophobic unit includes at least one vinyl carboxylate unit, and the vinyl carboxylate unit has 2 or more and 7 or less carbon atoms at a side chain terminal thereof.

Herein, the number of carbon atoms at the side chain terminal means the number of carbon atoms of a terminal hydrocarbon group bonded to a carbon atom of a side chain ester bond of the vinyl carboxylate unit. For example, a substance whose number of carbon atoms is 1 means vinyl acetate, and a substance whose number of carbon atoms is 2 means vinyl propanoate. The terminal hydrocarbon group may include not only a linear structure but also a branched structure such as an isopropyl group or a tertiary butyl group, a cyclic structure such as a cyclohexyl group or a phenyl group, or a heteroatom such as a nitrogen atom or an oxygen atom.

The term "unit" means a repeating unit in a (co)polymer obtained by polymerizing monomers. For example, a hydrophobic unit means a repeating unit in a (co)polymer obtained by polymerizing hydrophobic monomers. A vinyl carboxylate unit means a repeating unit in a (co)polymer obtained by polymerizing vinyl carboxylate monomers.

The term "hydrophobic unit" is defined as a repeating unit, a homopolymer of which (having a number average molecular weight of 30,000 or more and 50,000 or less) is hardly soluble or insoluble in water. Herein, "hardly soluble or insoluble in water" means that the relevant substance has a solubility of 1 g or less in 100 g of pure water at 20° C.

The term "hydrophilic unit" is defined as a repeating unit, a homopolymer of which (having a number average molecular weight of 30,000 or more and 50,000 or less) is easily soluble in water. Herein, "easily soluble in water" means that the relevant substance has a solubility exceeding 1 g, preferably 10 g or more in 100 g of pure water at 20° C.

The hydrophilic unit is not particularly limited, and examples thereof include repeating units derived from methacrylic acid, acrylic acid, 2-hydroxyethyl methacrylate, 2-hydroxyethyl acrylate, vinylpyrrolidone, vinyl alcohol, and ethylene glycol. Among them, a repeating unit derived from vinylpyrrolidone is preferred because the interaction with adsorbed water is not too strong and it is easy to keep the balance with a hydrophobic unit as compared with a unit having a hydroxyl group or a carboxylic acid group.

A different monomer such as a monomer including a reactive group such as a hydroxy group, a carboxy group, or a glycidyl group, may be copolymerized as long as the action and function of the copolymer are not inhibited.

The hydrophobic unit of the copolymer includes at least one vinyl carboxylate unit.

The number of carbon atoms at the side chain terminal of the vinyl carboxylate unit is 2 or more and 7 or less. Setting the number of carbon atoms at the side chain terminal of the vinyl carboxylate unit to 2 or more and 7 or less, preferably 2 or more and 6 or less, more preferably 2 or more and 4 or less makes it possible to control the mobility of adsorbed water and greatly improve the antithrombogenicity of the copolymer. If the number of carbon atoms at the side chain terminal of the vinyl carboxylate unit is too large, the hydrophobicity of the whole copolymer is strong so that platelets and proteins tend to adhere. On the other hand, if the number of carbon atoms is too small, blood coagulation or protein adhesion may occur with time when the copolymer is used in a medical device used in contact with a biological component such as blood for a long period of time as in a continuous renal replacement type blood purifier. More preferred as the vinyl carboxylate used in the vinyl carboxylate unit are vinyl propanoate (number of carbon atoms: 2), vinyl butyrate (number of carbon atoms: 3), vinyl pentanoate (number of carbon atoms: 4), and vinyl pivalate (number of carbon atoms: 4). The term "biological component" means a substance containing proteins, lipids, and carbohydrates of a living body, in addition to blood and body fluids constituting the living body.

If the number average molecular weight of the copolymer is too small, the effect of the copolymer may not be sufficiently exerted, and adhesion of platelets and proteins may become difficult to suppress when the copolymer is introduced onto the surface of a medical device. Thus, the number average molecular weight is preferably 2,000 or more, more preferably 3,000 or more. On the other hand, the upper limit of the number average molecular weight of the copolymer is not particularly limited, but the number average molecular weight is preferably 1,000,000 or less, more preferably 100,000 or less, even more preferably 50,000 or less, since the efficiency of introduction onto the surface of the medical device may decrease if the number average molecular weight is too large. The number average molecular weight of the copolymer is measured by gel permeation chromatography (GPC) as described later.

In the copolymer, the hydrophilic unit has a mole fraction to the whole copolymer of preferably 30% or more and 90% or less, more preferably 40% or more and 80% or less, even more preferably 50% or more and 70% or less. The range may be any combination of the above-mentioned upper limit and lower limit. If the mole fraction of the hydrophilic unit is too small, the hydrophobicity of the whole copolymer is strong so that adhesion of platelets and proteins is difficult to suppress. On the other hand, if the mole fraction is too large, the hydrophilicity of the whole copolymer is strong, the mobility of adsorbed water around the copolymer is reduced, and the structure of platelets and proteins becomes unstable so that adhesion is not suppressed. The mole fraction of the hydrophilic unit to the whole copolymer is calculated from the peak area as measured by nuclear magnetic resonance (NMR) measurement described later. If the mole fraction cannot be calculated by the NMR measurement for the reasons such as overlap of the peaks, the mole fraction may be calculated by elemental analysis.

Examples of the arrangement of the hydrophilic unit and the hydrophobic unit in the copolymer include a graft copolymer, a block copolymer, an alternating copolymer, and a random copolymer. Among them, a block copolymer, an alternating copolymer, and a random copolymer are preferred from the viewpoint of a high protein and platelet adhesion suppressing function, and a random copolymer and an alternating copolymer are more preferred from the viewpoint of an appropriate balance between hydrophilicity and hydrophobicity in one molecule. The reason why a block copolymer, an alternating copolymer, and a random copolymer are superior in the high protein and platelet adhesion suppressing function to a graft copolymer, for example, a graft copolymer having a main chain formed of a hydrophilic unit and a side chain formed of a hydrophobic unit, is considered as follows. In the graft copolymer, since the portion of the unit grafted to the main chain has many opportunities to come into contact with proteins or the like, the properties of the graft chain portion have a greater influence than the properties of the copolymerized polymer do. The reason why the alternating copolymer and the random copolymer are more preferred in view of an appropriate balance between hydrophilicity and hydrophobicity than the block copolymer is considered that the properties of the units (the hydrophilic part and the hydrophobic part) are more clearly divided in the block copolymer.

The copolymer can be synthesized, for example, by a chain polymerization method typified by a radical polymerization method using an azo type initiator, but the synthesis method is not limited thereto.

The medical device is mainly used in contact with a biological component such as blood or a body fluid. Specific examples of such a medical device include separation membrane modules for medical use that are used in a blood purifier, a plasma separator, and an artificial organ with a built-in separation membrane, a blood circuit, a blood storage bag, a catheter, and a stent.

The medical device includes the copolymer. Although there are various forms of utilization of the copolymer, it is preferred to introduce the copolymer onto at least a part of a surface in contact with a biological component such as blood (hereinafter sometimes referred to as blood or the like).

For example, immersing a flat membrane of polyethylene terephthalate used in an artificial blood vessel or the like in an aqueous solution of the copolymer can suppress adhesion of platelets. From the viewpoint of preventing thrombosis at the membrane surface, the number of adhered platelets per an area of $4.3 \times 10^3$ $\mu m^2$ is preferably 20 or less, more preferably 10 or less. The concentration of the aqueous solution of the copolymer is preferably 0.01 ppm or more, more preferably 0.1 ppm or more. The number of adhered platelets is measured by the method described later.

Moreover, the copolymer as a component for forming the separation membrane may be introduced onto the surface of the separation membrane (in particular, the inner surface which is often brought into contact with blood) to suppress the adhesion of blood components, and the separation membrane may be incorporated into a casing and used as a separation membrane module. The separation membrane is preferably in the form of a hollow fiber membrane. Herein, the separation membrane is a membrane that selectively removes certain substances contained in a liquid to be treated, such as blood or an aqueous solution, by adsorption or based on the size of the substances. Furthermore, in a blood circuit, the copolymer is preferably introduced onto an inner surface of a tube or the like constituting the circuit, which is mainly brought into contact with blood or the like. In a catheter, a stent or the like, it is conceivable to introduce the copolymer onto a surface of a (metal) material which is mainly brought into contact with blood or the like. "Introduce a copolymer onto a surface" means to place the copolymer on the surface of the object by a method such as coating or immersion. For example, in a separation membrane, a method of forming a membrane and then forming a coating of a copolymer is preferably used, and a method of bringing the copolymer as a solution (preferably an aqueous solution) into contact with the surface of the membrane is used. More specifically, there can be mentioned a method of flowing a solution of the copolymer at a predetermined flow rate, and a method of immersing the membrane in the solution. In addition, in a method of adding a copolymer to a stock solution for forming a membrane and spinning the stock solution, there is also a method of intentionally setting conditions so that the copolymer gathers on the membrane surface.

Furthermore, as a method of introducing the copolymer onto the surface of a medical device, covalent bonding by chemical reaction may be utilized. Specifically, the copolymer can be introduced onto the surface of a medical device by reacting a reactive group on the surface of the base material of the medical device such as a hydroxy group, a carboxy group, an amino group, a sulfonic acid group, or a halogenated alkyl group with a reactive group introduced into a main chain terminal or a side chain of the copolymer.

As a method of introducing a reactive group onto the surface of the base material, for example, there are a method of polymerizing a monomer having a reactive group to obtain a base material having a reactive group on the surface, and a method of introducing a reactive group by ozone treatment or plasma treatment after polymerization.

As a method of introducing a reactive group into the main chain terminal of the copolymer, for example, there is a method of using an initiator having a reactive group such as 2,2'-azobis[2-methyl-N-(2-hydroxyethyl)propionamide] or 4,4'-azobis(4-cyanovaleric acid).

As a method of introducing a reactive group into the side chain of the copolymer, for example, there is a method of copolymerizing a monomer having a reactive group such as glycidyl methacrylate or N-hydroxysuccinimide methacrylate ester as long as the action and function of the copolymer are not inhibited.

Examples of the polymer that can serve as a material of the medical device include a polysulfone-based polymer, polystyrene, polyurethane, polyethylene, polypropylene, polycarbonate, polyvinylidene fluoride, polyacrylonitrile, polymethyl methacrylate, polyvinyl chloride, and polyester, but are not limited thereto. Among them, a polysulfone-based polymer and polymethyl methacrylate are suitably used because they are easy to form a hollow fiber membrane and are easy to be coated with the copolymer, that is, an ester group-containing polymer.

It is more preferred that the hollow fiber membrane include a polysulfone-based polymer as a main raw material. The polysulfone-based polymer is a polymer having an aromatic ring, a sulfonyl group, and an ether group in the main chain, and examples thereof include polysulfone, polyether sulfone, and polyallyl ether sulfone. The "main raw material" means a raw material contained in an amount of 90% by weight or more based on the entire polysulfone-based polymer.

As the main raw material of the hollow fiber membrane, for example, a polysulfone-based polymer represented by chemical formulae (1) and/or (2) is suitably used, but the main raw material is not limited thereto. In the formulae, n is an integer of 1 or more, preferably 50 to 80. When n has a distribution, the average value is regarded as n.

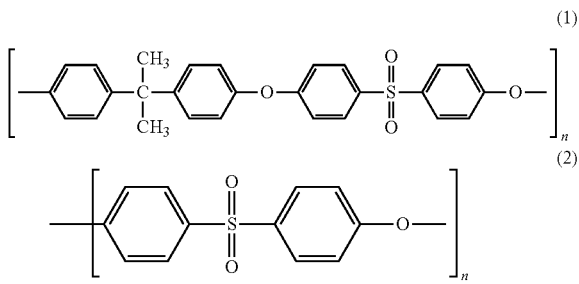

The polysulfone-based polymer that can be used in the separation membrane module for medical use is suitably a polymer composed only of the repeating units represented by the formulae (1) and/or (2), but the polysulfone-based polymer may be copolymerized with a different monomer or may be a modified product as long as the desired effect is not hindered. When the polysulfone-based polymer is copolymerized with a different monomer, the copolymerization rate of the different monomer is preferably 10% by weight or less based on the entire polysulfone-based polymer.

Specific examples of the polysulfone-based polymer that can be used in the separation membrane module for medical use include polysulfone-based polymers such as Udel Polysulfone P-1700 and P-3500 (manufactured by SOLVAY), Ultrason S3010 and S6010 (manufactured by BASF), VICTREX (manufactured by Sumitomo Chemical Co., Ltd.), Radel A (manufactured by SOLVAY), and Ultrason E (manufactured by BASF).

As a method of manufacturing the separation membrane module for medical use, there are various methods according to the use thereof. As rough processes, the manufacturing method can be divided into a step of manufacturing a separation membrane and a step of incorporating the separation membrane into a module. Furthermore, a treatment by radiation irradiation may be used before the step of incorporating the separation membrane into a module, or after the step of incorporating the separation membrane into a module. Performing a treatment by irradiation with γ-rays as a treatment by radiation irradiation after the step of incorporating the separation membrane into a module is preferred in that sterilization can be performed at the same time because the separation membrane module is intended for medical use.

An example of a method of manufacturing a hollow fiber membrane module used in a blood purifier will be described.

One example of a method of manufacturing a hollow fiber membrane incorporated into a blood purifier is the following method. That is, a stock solution (preferably having a concentration of 10 to 30% by weight, more preferably 15 to 25% by weight) obtained by dissolving polysulfone and polyvinylpyrrolidone (the weight ratio is preferably 20:1 to 1:5, more preferably 5:1 to 1:1) in a mixed solution of a good solvent for polysulfone (preferably N,N-dimethyl acetamide, dimethylsulfoxide, dimethylformamide, N-methylpyrrolidone, or dioxane) and a poor solvent therefor is discharged from a double annular spinneret while flowing an injection solution through the inside of the spinneret, and the stock solution and the injection solution are let to travel in a dry part and then led to a coagulation bath. At this time, since the humidity of the dry part has some influence, it is also possible to accelerate the phase separation behavior near the outer surface of the membrane by moisture supply from the outer surface during traveling of the membrane in the dry part to increase the pore diameter and, consequently, reduce the permeation/diffusion resistance during the dialysis. However, if the relative humidity is too high, the coagulation of the stock solution on the outer surface becomes dominant and the pore diameter rather decreases, which consequently tends to increase the permeation/diffusion resistance during the dialysis. Therefore, the relative humidity is suitably 60 to 90%. As for the composition of the injection solution, it is preferred to use a solution having a composition based on the solvent used for the stock solution from the viewpoint of process suitability. As for the concentration of the injection solution, for example, when dimethylacetamide is used, an aqueous solution having a concentration of 45 to 80% by weight, more preferably 60 to 75% by weight is suitably used.

The method of incorporating the hollow fiber membrane into a module is not particularly limited, and one example is as follows. First, the hollow fiber membrane is cut into a required length, required number of the membranes are bundled, and the bundle is placed in a cylindrical case. Then, the case is temporarily capped at both ends, and a potting agent is placed at both ends of the hollow fiber membranes. In this case, a method of placing a potting agent while rotating the module with a centrifuge is a preferred method because the potting agent is uniformly filled into the case. After the potting agent solidifies, both the ends of the hollow fiber membranes are cut so as to be opened to obtain a hollow fiber membrane module.

Since the polysulfone-based polymer used as a main raw material of the hollow fiber membrane is generally strongly hydrophobic, organic substances such as proteins are likely to adhere when the polymer is used as it is as a hollow fiber membrane. Therefore, in the separation membrane module for medical use, a hollow fiber membrane including the copolymer introduced onto the surface is suitably used. As a method of introducing the copolymer onto the surface, there are a method of bringing a solution in which the copolymer is dissolved into contact with a hollow fiber membrane in the module, and a method of bringing an injection solution containing the copolymer into contact with the inside of the hollow fiber membrane during spinning of the hollow fiber membrane.

When an aqueous solution in which the copolymer is dissolved is passed through a hollow fiber membrane in a module to introduce the copolymer onto the surface of the hollow fiber membrane, a sufficient amount of the copolymer is not introduced onto the surface if the copolymer concentration of the aqueous solution is too low. Therefore, the copolymer concentration of the aqueous solution is preferably 10 ppm or more, more preferably 100 ppm or more, even more preferably 300 ppm or more. However, if the copolymer concentration of the aqueous solution is too high, there is a concern that the amount of eluate from the module will increase. Therefore, the copolymer concentration of the aqueous solution is preferably 100,000 ppm or less, more preferably 10,000 ppm or less.

When the copolymer is hardly soluble or insoluble in water, it is possible to dissolve the copolymer in an organic solvent which does not dissolve the hollow fiber, or a mixed solvent of water and an organic solvent which is compatible with water and does not dissolve the hollow fiber. Specific examples of the organic solvent, or the organic solvent that can be used in the mixed solvent include alcohol solvents such as methanol, ethanol, and propanol, but are not limited thereto.

In addition, if the ratio of the organic solvent in the mixed solvent is large, the hollow fiber swells, the copolymer diffuses into the hollow fiber membrane, and it may become difficult to introduce the copolymer efficiently only onto the surface. Therefore, the weight fraction of the organic solvent in the mixed solvent is preferably 60% or less, more preferably 10% or less, even more preferably 1% or less.

In the separation membrane module for medical use to prevent elution of the introduced copolymer at the time of use of the module, it is preferred that the copolymer be insolubilized by radiation irradiation or heat treatment after being introduced onto the surface.

For the radiation irradiation, α-rays, β-rays, γ-rays, X-rays, ultraviolet rays, electron beams or the like can be used. For blood purifiers such as artificial kidneys, sterilization before shipping is mandatory. In recent years, radiation sterilization using γ-rays or electron beams is often used from the viewpoint of the low residual toxicity and convenience. Therefore, use of the radiation sterilization method in a state where an aqueous solution in which the copolymer is dissolved is in contact with the hollow fiber membrane in the separation membrane module for medical use is preferred because insolubilization of the copolymer can be achieved simultaneously with sterilization.

In simultaneously performing sterilization and reforming of the hollow fiber membrane in the separation membrane module for medical use, the irradiation dose of radiation is preferably 15 kGy or more, more preferably 25 kGy or more. This is because an irradiation dose of 15 kGy or more is effective for sterilizing a blood purification module or the like with γ-rays. The irradiation dose is preferably 100 kGy or less. If the irradiation dose exceeds 100 kGy, three-dimensional crosslinking and decomposition of the ester group moiety of the vinyl carboxylate unit are likely to occur in the copolymer, which may lower blood compatibility.

To suppress the crosslinking reaction upon irradiation with radiation, an antioxidant may be used. An antioxidant is a molecule having a property of easily giving electrons to other molecules. Specific examples thereof include water-soluble vitamins such as vitamin C, polyphenols, and alcohol solvents such as methanol, ethanol, and propanol, but are not limited thereto. These antioxidants may be used singly or in combination of two or more thereof. In using the antioxidant in the separation membrane module for medical use, safety should be considered. Therefore, an antioxidant with low toxicity is suitably used.

The amount of the copolymer introduced onto the surface of the hollow fiber membrane can be quantified by attenuated total reflection infrared spectroscopy (ATR-IR) as described later. Furthermore, if necessary, the amount can be quantified also by X-ray photoelectron spectroscopy (XPS) or the like. Herein, the surface of the hollow fiber membrane means the inner surface of the hollow fiber membrane that comes into contact with the blood.

When quantifying the surface introduction amount of the copolymer by ATR-IR, a ratio of the infrared absorption peak area ($A_{C=O}$) derived from the ester group C=O near 1730 $cm^{-1}$ to the infrared absorption peak area ($A_{C=C}$) derived from the benzene ring C=C of polysulfone near 1580 $cm^{-1}$, that is, ($A_{C=O}$)/($A_{C=C}$) is calculated at three different positions on the membrane surface. Measurement is made at arbitrary three positions in one hollow fiber membrane, and the average value thereof is regarded as the surface introduction amount of the copolymer. The ATR-IR is capable of measuring the surface up to several micrometers in depth.

To sufficiently suppress adhesion of proteins and platelets to the separation membrane module for medical use, the surface introduction amount of the copolymer is preferably 0.001 or more, more preferably 0.01 or more, even more preferably 0.03 or more.

The blood purifier includes the copolymer, and it is preferred that a separation membrane module for medical use be used as a blood purifier. A blood purifier refers to a medical device having a function of circulating the blood out of the body to remove waste products and harmful substances in the blood, and examples thereof include an artificial kidney module and an exotoxin adsorption column.

The blood purifier is excellent in blood compatibility and can maintain the property of suppressing platelet and protein adhesion for a long period of time due to use of the copolymer. Therefore, when the copolymer is used in a continuous renal replacement type blood purifier, the remarkable effect of the copolymer can be confirmed. Also in such a blood purifier, it is preferred that the copolymer be introduced onto at least a part of the surface in contact with a biological component such as blood.

The continuous renal replacement type blood purifier refers to a blood purifier that performs hemofiltration, hemodialysis, or hemodiafiltration over 8 hours or more.

The copolymer is manufactured by the following manufacturing method, but the method is not limited thereto.

Each predetermined amount of a hydrophilic monomer and a hydrophobic monomer, a polymerization solvent, and a polymerization initiator are mixed under stirring at a predetermined temperature for a predetermined period of time in a nitrogen atmosphere to cause a polymerization reaction. The quantitative ratio between the hydrophilic monomer and the hydrophobic monomer can be determined according to the mole fraction of the hydrophilic unit in the copolymer. The reaction liquid is cooled to room temperature to stop the polymerization reaction, and the liquid is charged into a solvent such as hexane. The deposited precipitate is collected and dried under reduced pressure to give a copolymer.

The polymerization reaction is preferably performed in a temperature range of 30° C. to 150° C., more preferably 50° C. to 100° C., even more preferably 70° C. to 80° C. The pressure is preferably normal pressure.

Preferably, the reaction time of the polymerization reaction is 1 hour or more, preferably 3 hours or more, more preferably 5 hours or more. If the reaction time is short, a large amount of unreacted monomer tends to remain in the copolymer. On the other hand, preferably, the reaction time is 24 hours or less, preferably 12 hours or less. If the reaction time is long, side reactions such as formation of dimers tend to occur, which may make it difficult to control the molecular weight.

In the polymerization reaction, the polymerization solvent is preferably a solvent compatible with the monomers. Examples thereof include ether solvents such as dioxane and tetrahydrofuran, amide solvents such as N,N-dimethylformamide, sulfoxide solvents such as dimethylsulfoxide, aromatic hydrocarbon solvents such as benzene and toluene, alcohol solvents such as methanol, ethanol, isopropyl alcohol, amyl alcohol, and hexanol, and water. Among these solvents, it is preferred to use an alcohol solvent or water for the low toxicity.

The polymerization initiator for the polymerization reaction may be a photopolymerization initiator or a thermal polymerization initiator. A polymerization initiator that generates any of a radical, a cation, and an anion may be used, but a radical polymerization initiator is suitably used from the viewpoint that it does not cause decomposition of the monomers. Examples of the radical polymerization initiator include azo type initiators such as azobisisobutyronitrile, azobisdimethylvaleronitrile, and dimethyl azobis(isobutyrate), and peroxide initiators such as hydrogen peroxide, benzoyl peroxide, di-tert-butyl peroxide, and dicumyl peroxide.

The solvent into which the polymerization reaction solution is charged after stopping of the polymerization reaction is preferably a solvent in which the copolymer precipitates. In particular, hydrocarbon solvents such as pentane, hexane, heptane, octane, nonane, and decane, and highly hydrophobic ether solvents such as dimethyl ether, ethyl methyl ether, diethyl ether, and diphenyl ether can be used.

To quantify adhesion of platelets and proteins, as described later, a temporal change of the sieving coefficient of albumin is measured. The sieving coefficient of albumin is determined by perfusing bovine blood into a separation membrane module for medical use including a copolymer introduced therein. Adhesion of platelets and proteins causes clogging of the pores of the hollow fibers so that the sieving coefficient of albumin reduces.

In blood purifiers such as artificial kidney modules, adhesion of proteins and platelets not only deteriorates fractionation performance and water permeability, but also inhibits blood circulation inside the hollow fibers due to blood coagulation, and extracorporeal circulation cannot be continued in some cases. The adhesion of platelets and proteins occurs particularly remarkably within 60 minutes after contact with blood. Thus, the sieving coefficients of albumin after 10 minutes and 60 minutes from the start of circulation of blood are measured, and the reduction rate is calculated.

The temporal change of the sieving coefficient of albumin is measured as follows. First, a hollow fiber membrane module (1) and a blood circuit are connected as shown in FIG. 1. Bovine blood supplemented with heparin is adjusted so that the hematocrit is 30% and the total protein concentration is 6 to 7 g/dl, and put in a circulation beaker (4). The circulation beaker (4) containing the bovine blood is kept at 37° C. in a warm water bath (9) equipped with a heater (8).

An inlet of a Bi circuit (5), an outlet of a Bo circuit (6), and an outlet of an F circuit (7) are placed in the circulation beaker (4) containing 2 L of the bovine blood adjusted as described above, and a Bi pump (2) is started at a circulation flow rate of 100 ml/min.

The Bi circuit (5) represents a flow path of blood which flows out from the circulation beaker (4), flows through the Bi pump (2), and enters a blood side inlet of the hollow fiber module (1). The Bo circuit (6) represents a flow path of blood which flows out from a blood side outlet of the hollow fiber module (1) and enters the circulation beaker (4). The F circuit (7) represents a flow path of blood which flows out from a dialysate side outlet of the hollow fiber module (1), flows through an F pump (3), and enters the circulation beaker (4). The Bi pump (2) represents a pump used for flowing blood through the Bi circuit (5).

Subsequently, the F pump (3) is started at a filtration flow rate of 10 ml/min, and the blood is sampled over time at the inlet of the Bi circuit (5), the outlet of the Bo circuit (6), and the outlet of the F circuit (7). Note that the F pump (3) represents a pump used for flowing blood through the F circuit (7).

The albumin concentration at each elapsed time from the start of the F pump (3) is measured, and the sieving coefficient of albumin (ScAlb) at each elapsed time is calculated according to formula (2).

$$\text{ScAlb (\%)} = CF/(CBi + CBo) \times 100 \tag{2}$$

In formula (2), CF represents the albumin concentration (g/ml) at the outlet of the F circuit (7), CBo represents the albumin concentration (g/ml) at the outlet of the Bo circuit (6), and CBi represents the albumin concentration (g/ml) at the inlet of the Bi circuit (5).

The reduction rate of the sieving coefficient of albumin after a perfusion time of 60 minutes (ScAlb60) to the sieving coefficient of albumin after a perfusion time of 10 minutes (ScAlb 10) was calculated according to formula (3).

$$\text{Reduction rate (\%)} = (\text{ScAlb10} - \text{ScAlb60})/\text{ScAlb10} \times 100 \tag{3}$$

At a site where a continuous renal replacement type blood purifier is used, it is desired that the blood purifier be replaced at every 24 hours or 48 hours to reduce the burden on the medical staff. Therefore, it is preferred that the blood purifier can be used for 24 hours, preferably for 48 hours.

In the separation membrane module for medical use in which the copolymer is introduced, the reduction rate of the sieving coefficient of albumin after a perfusion time of 60 minutes to the sieving coefficient of albumin after a perfusion time of 10 minutes is preferably 10% or less to keep using the blood purifier for 24 hours. Furthermore, to make it possible to use the blood purifier for 48 hours or more, it is more preferred that the reduction rate of the sieving coefficient of albumin be 5% or less.

Since the copolymer is excellent in blood compatibility and can maintain the property of suppressing protein adhesion for a long period of time, it is suitably used in medical devices. In particular, the copolymer is suitably used in a blood purifier, particularly a continuous renal replacement type blood purifier.

EXAMPLES

Hereinafter, our copolymers, medical devices, modules and purifiers will be described with reference to examples, but this disclosure is not limited to the examples.
Evaluation Methods
(1) Number Average Molecular Weight A 0.1 N $LiNO_3$ solution of water/methanol=50/50 (volume ratio) was adjusted and used as a GPC developing solution. In 2 ml of this solution, 2 mg of a copolymer was dissolved. Into a GPC connected to a column (Tosoh GMP-$W_{XL}$), 100 μL of the copolymer solution was injected. The flow rate was 0.5 mL/min, and the measurement time was 30 minutes. The detection was performed with a differential refractive index (RI) detector, and the number average molecular weight was calculated from the peak derived from the copolymer that appeared around the elution time of 15 minutes. The number average molecular weight was calculated by rounding off the number to the nearest thousand. A polyethylene oxide standard sample (0.1 kD to 1258 kD) manufactured by Agilent was used for preparing a calibration curve.
(2) Mole Fraction of Hydrophilic Unit In 2 ml of chloroform-D, 99.7% (containing 0.05 V/V % TMS, Wako Pure Chemical Industries), 2 mg of the copolymer was dissolved, and the solution was put in an NMR sample tube and subjected to NMR measurement. The temperature was set to room temperature, and the integration time was set to 32 times. From this measurement result, using the area of the region surrounded by the peak derived from the proton (3H) bonded to the carbon atom adjacent to the nitrogen atom of vinylpyrrolidone observed between 2.7 and 4.3 ppm and the baseline: $3A_{PVP}$, and the area of the region surrounded by the peak derived from the proton (1H) bonded to the carbon at the α-position of vinyl carboxylate observed between 4.3 and 5.2 ppm and the baseline: $A_{VC}$, the value of $A_{PVP}/(A_{PVP}+A_{VC})\times 100$ was calculated and regarded as the mole fraction of the vinylpyrrolidone unit. This method is an example of measuring the mole fraction in a copolymer of vinylpyrrolidone and vinyl carboxylate. In the case of a copolymer made of a combination of other monomers, peaks derived from appropriate protons are selected for the determination of the mole fraction. The mole fraction was calculated by rounding off the number to the nearest ten.
(3) Amount of Introduction of Copolymer onto Hollow Fiber Surface A hollow fiber membrane was trimmed to a semi-cylindrical shape with a microtome and fixed to a sample stage. Measurement was performed with a viewing angle, which is the range irradiated with infrared light (aperture), of 100 μm×100 μm, and an integration time of 30 times per point. The ratio of the peak area $A_{C=C}$ derived from the benzene ring double bond of the polysulfone near 1590 $cm^{-1}$ to the peak area $A_{C=O}$ derived from the ester bond of the vinyl carboxylate unit of the copolymer near 1730 $cm^{-1}$, that is, $A_{C=O}/A_{C=C}$ was calculated. Three positions of one hollow fiber were measured in hollow fibers of one module, and the average value was regarded as the amount of the copolymer introduced onto the surface of the hollow fiber. The average value was calculated by rounding off the number to two decimal places.

(4) Reduction Rate of Sieving Coefficient of Albumin

The reduction rate of the sieving coefficient of albumin was measured as follows. First, a hollow fiber membrane module (1) and a blood circuit were connected as shown in FIG. 1. Bovine blood supplemented with heparin was adjusted so that the hematocrit was 30% and the total protein concentration was 6 to 7 g/dl, and put in a circulation beaker (4). The circulation beaker (4) containing the bovine blood was kept at 37° C. in a warm water bath (9) equipped with a heater (8).

An inlet of a Bi circuit (5), an outlet of a Bo circuit (6), and an outlet of an F circuit (7) were placed in the circulation beaker (4) containing 2 L of the bovine blood adjusted as described above, and a Bi pump (2) was started at a circulation flow rate of 100 ml/min.

Subsequently, an F pump (3) was started at a filtration flow rate of 10 ml/min, and the blood was sampled over time at the inlet of the Bi circuit (5), the outlet of the Bo circuit (6), and the outlet of the F circuit (7).

The albumin concentration at each elapsed time from the start of the F pump (3) was measured, and the sieving coefficient of albumin (ScAlb) at each elapsed time was calculated according to the following formula.

$$ScAlb\ (\%)=CF/(CBi+CBo)\times 100$$

In the above formula, CF represents the albumin concentration (g/ml) at the outlet of the F circuit (7), CBo represents the albumin concentration (g/ml) at the outlet of the Bo circuit (6), and CBi represents the albumin concentration (g/ml) at the inlet of the Bi circuit (5).

The reduction rate of the sieving coefficient of albumin after a perfusion time of 60 minutes (ScAlb60) to the sieving coefficient of albumin after a perfusion time of 10 minutes (ScAlb10) was calculated according to the following formula. The reduction rate was calculated by rounding off the number to the nearest whole number.

$$\text{Reduction rate }(\%)=(ScAlb10-ScAlb60)/ScAlb10\times 100$$

(5) Platelet Adhesion Test Method for Flat Membrane for Medical Use

A double-sided tape was attached to a circular plate 18 mm in diameter made of polystyrene, and a flat membrane cut into a 0.5 cm square was fixed thereto. A flat membrane without any contaminant, scratch, or crease was used because platelets may adhere to the flat membrane surface and hinder correct evaluation if there is any contaminant, scratch, or crease. The circular plate was attached to a cylindrically cut FALCON (registered trademark) tube (18 mm in diameter, No. 2051) so that the face to which the flat membrane was attached was inside of the cylinder, and the gap was filled with Parafilm. The inside of this cylindrical tube was washed with physiological saline, and then the tube was filled with physiological saline. Human venous blood was collected, and heparin was added to the blood immediately after the collection so that the concentration would be 50 U/ml. The physiological saline in the cylindrical tube was discharged, and then 1.0 ml of the blood was put in the cylindrical tube within 10 minutes after the blood collection and shaken at 37° C. for 1 hour. Then, the flat membrane was washed with 10 ml of physiological saline, and blood components were fixed with 2.5% glutaraldehyde physiological saline and washed with 20 ml of distilled water. The washed flat membrane was dried under reduced pressure at 20° C. and 0.5 Torr for 10 hours. This flat membrane was attached to a sample stage of a scanning electron microscope with a double-sided tape. After that, a Pt—Pd thin film was formed on the flat membrane surface by sputtering to prepare a sample. The inner surface of the flat membrane sample was observed with a field emission type scanning electron microscope (S800 manufactured by Hitachi, Ltd.) at a magnification of 1500 times, and the number of adhered platelets in one field of view ($4.3 \times 10^3$ μm$^2$) was counted. When 50 or more platelets adhered, it was assumed that no platelet adhesion suppression effect was exerted, and the number of adhered platelets was regarded as 50. The average value of the number of adhered platelets in 20 different fields of view near the center of the flat membrane was regarded as the number of adhered platelets (number/$4.3 \times 10^3$ μm$^2$).

Method of Manufacturing Hollow Fiber Membrane Module

To 72 parts by weight of N,N-dimethylacetamide and 1 part by weight of water, 18 parts by weight of polysulfone (Udel P-3500 manufactured by Teijin Amoco) and 9 parts by weight of polyvinylpyrrolidone (K30 manufactured by BASF) were added, and the mixture was heated at 90° C. for 14 hours for dissolution. This membrane-forming stock solution was discharged from an orifice-type double cylindrical spinneret having an outer diameter of 0.3 mm and an inner diameter of 0.2 mm, and a solution of 57.5 parts by weight of N,N-dimethylacetamide and 42.5 parts by weight of water was discharged as a core liquid, the membrane-forming stock solution and the core liquid were passed through a dry part having a length of 350 mm, and led to a coagulation bath of 100% water to give a hollow fiber. The obtained hollow fiber had an inner diameter of 200 μm and a thickness of 40 μm. The hollow fiber membrane was filled in a case so as to have an inner surface area of 1.0 m$^2$, potted, and ends were opened at both sides to give a hollow fiber membrane module.

Example 1

A vinylpyrrolidone/vinyl propanoate random copolymer was prepared by the following method. That is, 19.5 g of a vinylpyrrolidone monomer, 17.5 g of a vinyl propanoate monomer, 56 g of t-amyl alcohol as a polymerization solvent, and 0.175 g of 2,2'-azobis(2,4-dimethylvaleronitrile) as a polymerization initiator were mixed, and the mixture stirred at 70° C. for 6 hours in a nitrogen atmosphere. The reaction liquid was cooled to room temperature to stop the reaction, concentrated, and then charged into hexane. The deposited white precipitate was collected and dried under reduced pressure to give 21.0 g of a copolymer. From the result of $^1$H-NMR, we found that the mole fraction of the vinylpyrrolidone unit was 60%. Furthermore, from the measurement result of GPC, the number average molecular weight Mn of the copolymer was 16,500.

A separation membrane module for medical use, in which the prepared vinylpyrrolidone/vinyl propanoate random copolymer was introduced onto the surface of the polysulfone hollow fiber, was produced by the following method. A 1.0 wt % aqueous ethanol solution in which 300 ppm of the copolymer was dissolved was passed from the blood side inlet to the dialysate side inlet of the hollow fiber membrane module produced by the above-mentioned manufacturing method. Furthermore, a 0.1 wt % aqueous ethanol solution was passed from the blood side inlet to the dialysate side inlet of the hollow fiber membrane module and from the blood side inlet to the blood side outlet thereof, and the module was irradiated with 25 kGy γ-rays to produce a separation membrane module for medical use. From the measurement results of ATR-IR, we found that the introduction amount (area ratio) of the copolymer on the inner surface of the hollow fiber was 0.06 on average. The sieving coefficient of albumin of the produced separation membrane module for medical use was measured. As a result, as shown in Table 1, the reduction rate of the sieving coefficient of albumin after a perfusion time of 60 minutes to the sieving coefficient of albumin after a perfusion time of 10 minutes was 2%.

TABLE 1

|  | Example 1 | Example 2 | Example 3 | Example 4 | Example 5 | Example 6 | Example 7 |
| --- | --- | --- | --- | --- | --- | --- | --- |
| Hydrophilic unit | Vinylpyrrolidone | Vinylpyrrolidone | Vinylpyrrolidone | Vinylpyrrolidone | Vinyl caprolactam | Vinylpyrrolidone | Vinylpyrrolidone |
| Hydrophobic unit | Vinyl propanoate | Vinyl propanoate | Vinyl pivalate | Vinyl butyrate | Vinyl propanoate | Vinyl benzoate | Vinyl 2-ethylhexanoate |
| Number of carbon atoms at side chain terminal | 2 | 2 | 4 | 3 | 2 | 6 | 7 |
| Number average molecular weight | 16,500 | 16,500 | 3,900 | 2,100 | 20,800 | 2,900 | 4,500 |
| Mole fraction of vinylpyrrolidone unit (%) | 60 | 60 | 70 | 60 | 70 | 80 | 80 |
| Filling concentration (ppm) | 300 | 200 | 300 | 300 | 300 | 300 | 300 |
| Reduction rate of sieving coefficient of albumin (%) | 2 | 4 | 3 | 9 | 7 | 8 | 8 |

Example 2

A separation membrane module for medical use was produced in the same manner as in Example 1 except that the concentration of the aqueous ethanol solution of the vinylpyrrolidone/vinyl propanoate random copolymer was changed to 200 ppm, and the sieving coefficient of albumin measured. As a result, as shown in Table 1, the reduction rate of the sieving coefficient of albumin after a perfusion time of 60 minutes to the sieving coefficient of albumin after a perfusion time of 10 minutes was 4%. Furthermore, from the measurement results of ATR-IR, we found that the introduction amount (area ratio) of the copolymer on the inner surface of the hollow fiber was 0.05 on average.

Example 3

A separation membrane module for medical use was produced in the same manner as in Example 1 except that a vinylpyrrolidone/vinyl pivalate random copolymer (vinylpyrrolidone unit mole fraction: 70%, number average molecular weight: 3,900) was used in place of the vinylpyrrolidone/vinyl propanoate random copolymer, and the sieving coefficient of albumin measured. As a result, as shown in Table 1, the reduction rate of the sieving coefficient of albumin after a perfusion time of 60 minutes to the sieving coefficient of albumin after a perfusion time of 10 minutes was 3%.

Example 4

A separation membrane module for medical use was produced in the same manner as in Example 1 except that a vinylpyrrolidone/vinyl butyrate random copolymer (vinylpyrrolidone unit mole fraction: 60%, number average molecular weight: 2,100) was used in place of the vinylpyrrolidone/vinyl propanoate random copolymer, and the sieving coefficient of albumin measured. As a result, as shown in Table 1, the reduction rate of the sieving coefficient of albumin after a perfusion time of 60 minutes to the sieving coefficient of albumin after a perfusion time of 10 minutes was 9%.

Example 5

A separation membrane module for medical use was produced in the same manner as in Example 1 except that a vinyl caprolactam/vinyl propanoate random copolymer (vinyl caprolactam mole fraction: 70%, number average molecular weight: 20,800) was used in place of the vinylpyrrolidone/vinyl propanoate random copolymer, and the sieving coefficient of albumin measured. As a result, as shown in Table 1, the reduction rate of the sieving coefficient of albumin after a perfusion time of 60 minutes to the sieving coefficient of albumin after a perfusion time of 10 minutes was 7%.

Example 6

A separation membrane module for medical use was produced in the same manner as in Example 1 except that a vinylpyrrolidone/vinyl benzoate random copolymer (vinylpyrrolidone unit mole fraction: 80%, number average molecular weight: 2,900) was used in place of the vinylpyrrolidone/vinyl propanoate random copolymer, and the sieving coefficient of albumin measured. As a result, as shown in Table 1, the reduction rate of the sieving coefficient of albumin after a perfusion time of 60 minutes to the sieving coefficient of albumin after a perfusion time of 10 minutes was 8%.

Example 7

A separation membrane module for medical use was produced in the same manner as in Example 1 except that a vinylpyrrolidone/vinyl 2-ethylhexanoate random copolymer (vinylpyrrolidone unit mole fraction: 80%, number average molecular weight: 4,500) was used in place of the vinylpyrrolidone/vinyl propanoate random copolymer, and the sieving coefficient of albumin measured. As a result, as shown in Table 1, the reduction rate of the sieving coefficient of albumin after a perfusion time of 60 minutes to the sieving coefficient of albumin after a perfusion time of 10 minutes was 8%.

Comparative Example 1

A separation membrane module for medical use was produced in the same manner as in Example 1 except that no copolymer was introduced, and the sieving coefficient of albumin measured. As a result, as shown in Table 2, the reduction rate of the sieving coefficient of albumin after a perfusion time of 60 minutes to the sieving coefficient of albumin after a perfusion time of 10 minutes was 70%.

TABLE 2

|  | Comparative Example 1 | Comparative Example 2 | Comparative Example 3 | Comparative Example 4 | Comparative Example 5 | Comparative Example 6 |
| --- | --- | --- | --- | --- | --- | --- |
| Hydrophilic unit | — | Vinylpyrrolidone | Vinylpyrrolidone | Vinylpyrrolidone | Vinylpyrrolidone | Vinylpyrrolidone |
| Hydrophobic unit | — | — | Vinyl acetate | Vinyl acetate | Vinyl decanoate | Vinyl nonanoate |
| Number of carbon atoms at side chain terminal | — | 0 | 1 | 1 | 9 | 8 |
| Number average molecular weight | — | 360,000 | 3,900 | 3,900 | 19,000 | 4,400 |
| Mole fraction of vinylpyrrolidone unit (%) | — | 100 | 60 | 60 | 80 | 80 |
| Filling concentration (ppm) | — | 300 | 300 | 200 | 300 | 300 |
| Reduction rate of sieving coefficient of albumin (%) | 70 | 60 | 15 | 23 | 17 | 25 |

Comparative Example 2

A separation membrane module for medical use was produced in the same manner as in Example 1 except that polyvinylpyrrolidone ("K90" manufactured by BASF) was used in place of the vinylpyrrolidone/vinyl propanoate random copolymer, and the sieving coefficient of albumin measured. As a result, as shown in Table 2, the reduction rate of the sieving coefficient of albumin after a perfusion time of 60 minutes to the sieving coefficient of albumin after a perfusion time of 10 minutes was 60%.

Comparative Example 3

A separation membrane module for medical use was produced in the same manner as in Example 1 except that a vinylpyrrolidone/vinyl acetate random copolymer ("Kollidon VA64" manufactured by BASF) was used in place of the vinylpyrrolidone/vinyl propanoate random copolymer, and the sieving coefficient of albumin measured. As a result, as shown in Table 2, the reduction rate of the sieving coefficient of albumin after a perfusion time of 60 minutes to the sieving coefficient of albumin after a perfusion time of 10 minutes was 15%.

Comparative Example 4

A separation membrane module for medical use was produced in the same manner as in Comparative Example 3 except that the concentration of the vinylpyrrolidone/vinyl acetate random copolymer ("Kollidon VA64" manufactured by BASF) was changed to 200 ppm, and the sieving coefficient of albumin measured. As a result, as shown in Table 2, the reduction rate of the sieving coefficient of albumin after a perfusion time of 60 minutes to the sieving coefficient of albumin after a perfusion time of 10 minutes was 23%.

Comparative Example 5

A separation membrane module for medical use was produced in the same manner as in Example 1 except that a vinylpyrrolidone/vinyl decanoate random copolymer (vinylpyrrolidone unit mole fraction: 80%, number average molecular weight: 19,000) was used in place of the vinylpyrrolidone/vinyl propanoate random copolymer, and the sieving coefficient of albumin measured. As a result, as shown in Table 2, the reduction rate of the sieving coefficient of albumin after a perfusion time of 60 minutes to the sieving coefficient of albumin after a perfusion time of 10 minutes was 17%.

Comparative Example 6

A separation membrane module for medical use was produced in the same manner as in Example 1 except that a vinylpyrrolidone/vinyl nonanoate random copolymer (vinylpyrrolidone unit mole fraction: 80%, number average molecular weight: 4,400) was used in place of the vinylpyrrolidone/vinyl propanoate random copolymer, and the sieving coefficient of albumin measured. As a result, as shown in Table 2, the reduction rate of the sieving coefficient of albumin after a perfusion time of 60 minutes to the sieving coefficient of albumin after a perfusion time of 10 minutes was 25%.

Method of Manufacturing Flat Membrane

A polyethylene terephthalate film (manufactured by Toray Industries, Inc.) having a thickness of 5 μm was cut into a 5 cm² piece and placed in a 15 mL centrifuge tube (manufactured by AS ONE Corporation). The interior of the centrifuge tube was filled with an aqueous copolymer solution having a concentration of 0.1 ppm, the tube was covered, and the film was irradiated with 25 kGy γ-rays to give a flat membrane.

Example 8

A flat membrane was produced by using a vinylpyrrolidone/vinyl propanoate random copolymer (vinylpyrrolidone unit mole fraction: 60%, number average molecular weight: 16,500) as the copolymer according to the above-mentioned manufacturing method of flat membrane. As a result of platelet adhesion test of the obtained flat membrane, as shown in Table 3, the number of adhered platelets was 9, and we found that adhesion of platelets was largely suppressed.

TABLE 3

|  | Example 8 | Comparative Example 7 | Comparative Example 8 | Comparative Example 9 |
| --- | --- | --- | --- | --- |
| Hydrophilic unit | Vinylpyrrolidone | — | Vinylpyrrolidone | Vinylpyrrolidone |
| Hydrophobic unit | Vinyl propanoate | — | — | Vinyl acetate |
| Number of carbon atoms at side chain terminal | 2 | — | 0 | 1 |
| Number average molecular weight | 16,500 | — | 12,000 | 3,900 |
| Mole fraction of vinylpyrrolidone unit (%) | 60 | — | 100 | 60 |
| Number of adhered platelets (number) | 9 | 46 | 42 | 38 |

Comparative Example 7

A flat membrane was produced in the same manner as in Example 8 except that no copolymer was used, and a platelet adhesion test was conducted. As a result, as shown in Table 3, the number of adhered platelets was 46, and we found that a large number of platelets adhered.

Comparative Example 8

A flat membrane was produced in the same manner as in Example 8 except that polyvinylpyrrolidone ("K30" manufactured by BASF) was used in place of the vinylpyrrolidone/vinyl propanoate random copolymer, and a platelet adhesion test was conducted. As a result, as shown in Table 3, the number of adhered platelets was 42, and we found that a large number of platelets adhered.

Comparative Example 9

A flat membrane was produced in the same manner as in Example 8 except that a vinylpyrrolidone/vinyl acetate random copolymer ("Kollidon VA64" manufactured by BASF) was used in place of the vinylpyrrolidone/vinyl propanoate random copolymer, and a platelet adhesion test was conducted. As a result, as shown in Table 3, the number of adhered platelets was 38, and we found that a large number of platelets adhered.

The invention claimed is:
1. A copolymer comprising a hydrophilic unit and a hydrophobic unit, wherein the hydrophobic unit includes at least one vinyl carboxylate unit, and the vinyl carboxylate unit has 2 or more and 7 or less carbon atoms at a side chain terminal thereof, wherein the hydrophilic unit includes a vinylpyrrolidone unit.

2. The copolymer according to claim 1, having a number average molecular weight of 2,000 or more.

3. The copolymer according to claim 1, wherein the hydrophilic unit has a mole fraction to the whole copolymer of 30% or more and 90% or less.

4. The copolymer according to claim 1, wherein the hydrophilic unit and the hydrophobic unit are arranged randomly or alternately.

5. A medical device comprising a copolymer comprising a hydrophilic unit and a hydrophobic unit, wherein the hydrophobic unit includes at least one vinyl carboxylate unit, and the vinyl carboxylate unit has 2 or more and 7 or less carbon atoms at a side chain terminal thereof, comprising the copolymer introduced onto at least a part of a surface thereof that is in contact with a biological component.

6. A separation membrane module for medical use, comprising a separation membrane including a copolymer comprising a hydrophilic unit and a hydrophobic unit, wherein the hydrophobic unit includes at least one vinyl carboxylate unit, and the vinyl carboxylate unit has 2 or more and 7 or less carbon atoms at a side chain terminal thereof.

7. The separation membrane module according to claim 6, wherein the separation membrane includes a polysulfone-based polymer as a main raw material.

8. A blood purifier comprising a copolymer comprising a hydrophilic unit and a hydrophobic unit, wherein the hydrophobic unit includes at least one vinyl carboxylate unit, and the vinyl carboxylate unit has 2 or more and 7 or less carbon atoms at a side chain terminal thereof.

9. The blood purifier according to claim 8, which is a continuous renal replacement.

10. The blood purifier according to claim 8, comprising the copolymer introduced onto at least a part of a surface thereof that is in contact with blood or a biological component.

11. The blood purifier according to claim 9, comprising the copolymer introduced onto at least a part of a surface thereof that is in contact with blood or a biological component.

12. The copolymer according to claim 2, wherein the hydrophilic unit has a mole fraction to the whole copolymer of 30% or more and 90% or less.

13. The copolymer according to claim 2, wherein the hydrophilic unit and the hydrophobic unit are arranged randomly or alternately.

14. The copolymer according to claim 3, wherein the hydrophilic unit and the hydrophobic unit are arranged randomly or alternately.

* * * * *